US007086611B2

(12) United States Patent
Grausam

(10) Patent No.: US 7,086,611 B2
(45) Date of Patent: Aug. 8, 2006

(54) DEVICE FOR PRODUCING AN AEROSOL

(76) Inventor: Ingo Grausam, Teckstrasse 15, 73230 Kirchheim/Teck (DE)

( * ) Notice: Subject to any disclaimer, the term of this patent is extended or adjusted under 35 U.S.C. 154(b) by 0 days.

(21) Appl. No.: 10/968,836

(22) Filed: Oct. 19, 2004

(65) Prior Publication Data

US 2006/0081724 A1 Apr. 20, 2006

(51) Int. Cl.
*A61M 11/06* (2006.01)
*A01G 27/00* (2006.01)
*B05B 7/32* (2006.01)
*F23D 11/24* (2006.01)
*F23D 14/28* (2006.01)

(52) U.S. Cl. ........................ 239/338; 239/337; 239/67; 239/68

(58) Field of Classification Search ................ 239/338, 239/337, 67, 68, 69, 340, 352, 353, 372, 239/373; 184/55.1, 54
See application file for complete search history.

(56) References Cited

U.S. PATENT DOCUMENTS 3,939,944 A * 2/1976 Mitchell et al. ........... 184/6.26
4,353,435 A * 10/1982 Abrams et al. ............ 184/6.26
5,806,630 A * 9/1998 Bernal ....................... 184/6.26
6,622,942 B1 * 9/2003 Ueno et al. ................. 239/311
2002/0084146 A1 * 7/2002 Itoh ............................ 184/57
2004/0124265 A1 7/2004 Kaelberer ................... 239/338

FOREIGN PATENT DOCUMENTS

DE 19917219 10/2000 .................... 11/10
DE 10139950 7/2003 ........................ 3/4
EP 0 941 769 * 9/1999
WO WO 98/10217 * 3/1998

* cited by examiner

*Primary Examiner*—David A. Scherbel
*Assistant Examiner*—Darren Gorman
(74) *Attorney, Agent, or Firm*—O'Shea, Getz & Kosakowski, P.C.

(57) ABSTRACT

A device for producing an aerosol is provided that includes a gas infeed line, an aerosol container, a plurality of nozzles, a differential pressure sensor, a plurality of valves, and a control unit. The plurality of nozzles are located within the aerosol container, and are in fluid communication with the gas infeed line. The differential pressure sensor determines the difference between a first pressure within the gas infeed line, and a second pressure within the aerosol container. The plurality of valves are in fluid communication with the gas infeed line. The control unit is in communication with the plurality of valves. The plurality of nozzles are controllable independent of one another, using the valves. The control unit determines and sets a combination of the plurality of nozzles, using a signal from the differential pressure sensor, to substantially maintain the second pressure within the aerosol container at a predetermined level.

7 Claims, 1 Drawing Sheet

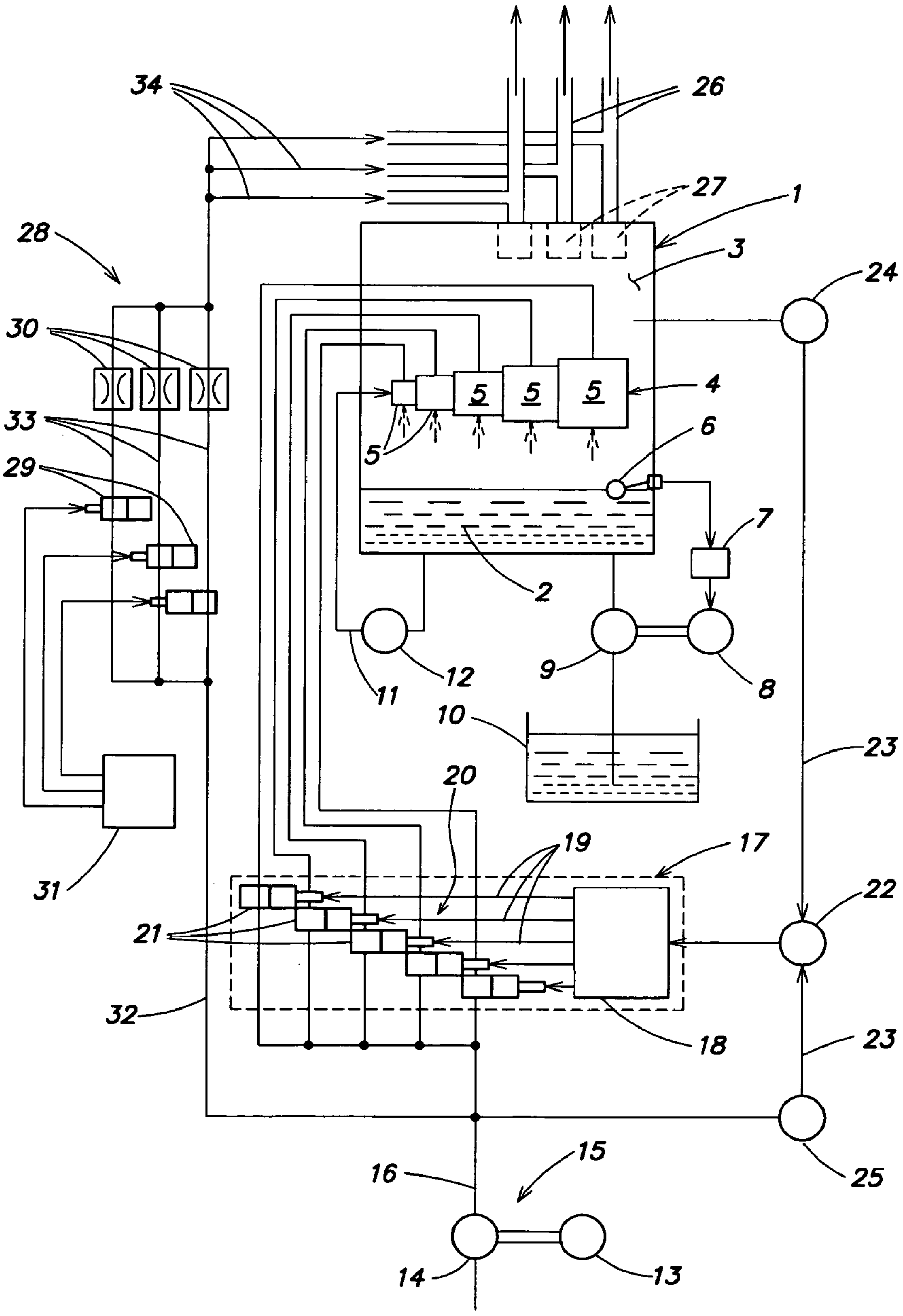
34
26
27
1
28
3
24
30
4
5
5
5
33
5
6
29
7
2
9
8
12
11
10
23
20
19
17
31
21
22
32
18
23
15
16
25
14
13

DEVICE FOR PRODUCING AN AEROSOL

BACKGROUND OF THE INVENTION

1. Technical Field

This invention relates to a device for producing an aerosol from a gas and a liquid by atomizing the same within at least one nozzle located in a pressurized aerosol container and with a differential pressure sensor that determines the difference between the pressure in a gas infeed line and the pressure within the pressurized aerosol container.

2. Background Information

German Patent No. DE 101 39 950 A1 discloses a device for producing an aerosol from a gas and a liquid. The aerosol produced is available in a pressurized aerosol container at a given pressure above a liquid level, for example for lubricating and cooling cutting tools in lathes or milling machines. A differential pressure sensor serves to turn off an infeed of liquid (e.g., oil) and infeed of compressed gas (e.g., air) when a pressure differential is below a given minimum. However, this device is not able to smooth out variations in the compressed air supply, and lacks desired stability. Thus, it has been found that the internal pressure in the container can vary by about 1.5 bar when small volumes are withdrawn, so that it is between 2.5 bar and 4 bar. However, the amount of aerosol supplied to the user is then also subject to these variations. This is undesirable.

The optimal spraying action of an atomizer nozzle in which the aerosol is produced with minimal particle size depends on the design of the atomizer nozzle and is achieved at a given flow velocity of the atomizer air and a given throughput of air. In the aforementioned device, the atomizer nozzle works against the internal pressure of the pressurized aerosol container. Thus, the air throughput is determined by the pressure differential between the supplied compressed air and the internal pressure of the pressurized aerosol container, and thus changes with it. It has now been found that with the aforementioned device, particularly with severely varying withdrawal of aerosol, the atomizer nozzle very often does not operate in its optimal range, which is at a pressure differential of about 2 bar, for example. This then leads to the aerosol produced not having the desired minimal particle size. There is then the risk that the aerosol will partly separate out on the way to the point of use. This results in the liquid depositing within the nozzle, forming drops that block the flow of aerosol within the nozzle which aerosol is then not available at the point of use, or not in the required amount.

SUMMARY OF THE INVENTION

Accordingly, it is an object of the present invention to provide a device that can produce desirable aerosol under all operating conditions of the aerosol apparatus. The present invention provides a bank of graduated atomizer nozzles that can be operated individually and independently of one another, or jointly, and that controls the unthrottled supply of compressed air to the atomizer nozzles by valves. A control device, puts in operation the atomizer nozzle(s) whose throughput volume(s) will maintain the desired internal pressure in the pressurized container, even with varying withdrawal of aerosol. The present invention consequently operates at a desirable pressure differential; this provides the benefit that the atomizer nozzles are impacted with the full supply pressure of compressed air and accordingly operate in the aforesaid operating range, producing aerosol with favorable particle size.

These and other objects, features and advantages of the present invention will become apparent in light of the drawing and detailed description of the present invention provided below.

BRIEF DESCRIPTION OF THE DRAWINGS

The drawing is a block diagram of the aerosol device.

DETAILED DESCRIPTION OF THE INVENTION

Referring to the drawing, the core component of the device for producing aerosol is a pressurized aerosol container 1 that is filled with the liquid medium 2, (e.g., oil), up to a certain height, from which the aerosol is to be produced. According to the invention, there is a bank 4 of atomizer (Venturi, injector) nozzles 5 in a space 3 above the liquid level, in which the liquid medium is atomized with the introduction of compressed gas, (e.g., compressed air), atomized into fine droplets that are carried by the compressed gas and constitute the aerosol. In the example provided the bank 4 includes five atomizer nozzles 5—it is to be understood, however, that the bank 4 can also include fewer or more nozzles.

The pressurized aerosol container 1 can have a level sensor 6 with a control device 7 that turns on a motor 8, which feeds liquid medium with a pump 9 from a supply container 10 to the pressurized container when the liquid medium level drops in the pressurized container.

The bank 4 of atomizer nozzles 5 includes nozzles with different rated throughput volumes relative to the optimal operating point of the nozzles. The rated throughput volumes of the nozzles preferably follow a geometric sequence; for example they are in the ratios 1:2:4:8:16. With this bank 4 of atomizer nozzles 5, thirty-one (31) stages of aerosol production volumes can be set by turning nozzles on or off.

The medium is drawn by suction in the particular amount required by the injector action of the atomizer nozzles 5, from the pressurized aerosol container 1 through a line 11, in which there can be an in-line flow meter 12. The infeed of medium is therefore not usually throttled; the atomizer nozzles draw in the optimal amount of medium for their atomizer action, by themselves and in a self-regulating manner.

The required compressed air can be supplied by a pressure source 15 through a compressed air line 16, which pressure source is shown in the drawing as including a motor 13 and a pump 14. However, other sources of compressed-air may be used alternatively.

A control device 17 contains a control unit 18 by which a battery 20 of individually and separately controllable 2/2-way valves 21 of the same kind can be accessed through control lines 19. The control unit 18 in turn is accessed by a differential pressure device 22 that is connected to pressure sensor 24. The pressure device 22 is connected through lines 23 to the interior of the pressurized container 1, and to a pressure sensor 25, which is connected to the compressed air line 16. The control unit 18 contains a control algorithm that can determine and control, through the 2/2-way valves 21, the combination of active atomizer nozzles 5 in their desired operating range, using the measurement signal from the pressure differential device 22; i.e., the internal pressure in the pressurized container can be maintained at the desired level even with varying withdrawal of aerosol, by using the pressure differential between the compressed air line 16 and the pressurized container 1. The compressed air is fed to the nozzles 5 without throttling, and they are therefore supplied with the full optimal pressure, so that they are actively maintained in their optimal operating range.

The aerosol produced in the pressurized aerosol container 1 under pressure above the liquid level is available for use, for example for lubricating and cooling cutting tools in lathes or milling machines. It can be tapped through one or more tap lines 26. Ahead of the tap lines 26 are separating devices 27 in the form of screen cages in which aerosol particles that are too large are deposited.

When a rise in the internal pressure in the pressurized container 1 above the intended threshold is reported to the control unit 18 of the control device 17, or it is reported that the pressure differential has dropped below the minimum, the present invention adapts the operation of the atomizer nozzles 5 by reversing the 2/2-way valves 21 through the lines 19. In this way, for example, it turns off atomizing nozzles 5 in case of rising pressure in the pressurized container 1, or changes from the operation of atomizing nozzles with larger throughput volumes to those with lower throughput volumes, or vice versa. This makes it possible to achieve production of aerosol with uniform saturation constant small particle size, and constant internal pressure within the pressurized container.

As mentioned, the nozzles 5 operate with desirable throughput of medium. When an aerosol concentration is thereby formed that is too high for certain applications, additional aerosol-free air can be fed to the tap lines 26, which reduces the aerosol concentration.

A device 28 for controllable infeed of compressed air is provided for this purpose; it comprises the valves 29 and throttles 30, as well as a control device 31. Compressed air is fed through a branch line 32 coming from the compressed air line 16 to the parallel valves 29—three in this case—in the secondary lines 33 and to the three throttles 30 in series with each of them. The device 28 is not limited to three valves and/or throttles, however. The throttling action of the three throttles 30 is graduated. The volume of the stream of aerosol-free additional air that is to be fed to the tap lines 26 can be set on the control device 31, and the control device accordingly impacts one or more of the valves 29 and thus opens up the correct quantity of compressed air inflow through one or more of the subsidiary lines 33. The subsidiary lines 33 are recombined downstream from the throttles 30 and with them the substreams, which flow through branch lines 34 to the tap lines 26.

It should be understood that, instead of admixing air, the liquid medium concentration in the aerosol can also be reduced by reducing the intake of liquid medium through the nozzles by suction by adjustable or on-off controllable throttles inserted in its feed line, and the aerosol can thereby be made leaner. It is also possible to combine the admixing of air and the throttling of medium infeed for this purpose.

Although this invention has been shown and described with respect to the detailed embodiments thereof, it will be understood by those skilled in the art that various changes in form and detail thereof may be made without departing from the spirit and scope of the invention.

What is claimed is:

1. A device for producing an aerosol from a gas and a liquid by atomizing the liquid with at least one nozzle located in a pressurized aerosol container, and including a differential pressure sensor that determines the difference between a pressure in a gas infeed line and the pressure in the pressurized aerosol container, and depending on this, turns on or off the infeed of the gas to the nozzle, comprising a plurality of nozzles that are provided in the pressurized aerosol container that are controllable independently of one another by valves, and that from the measurement signal from the differential pressure sensor, a control unit determines and sets a combination of nozzles that maintains the pressure in the pressurized aerosol container at a desired level without throttling the nozzles.

2. A device according to claim 1, wherein the rated throughput volumes of the nozzles are graduated.

3. A device according to claim 1, further comprising a plurality of tap lines extending into the aerosol container, and a device with which aerosol-free gas can optionally be fed into the tap lines of the aerosol container.

4. A device for producing an aerosol, comprising:

a gas infeed line;

an aerosol container;

a plurality of nozzles located within the aerosol container, and in fluid communication with the gas infeed line;

a differential pressure sensor that determines the difference between a first pressure within the gas infeed line, and a second pressure within the aerosol container;

a plurality of valves in fluid communication with the gas infeed line;

a control unit in communication with the plurality of valves, wherein the plurality of nozzles are controllable independent of one another, using the valves; and wherein the control unit determines and sets a combination of the plurality of nozzles, using a signal from the differential pressure sensor, to substantially maintain the second pressure within the aerosol container at a predetermined level.

5. The device of claim 4, wherein the plurality of nozzles have graduated rated throughput volumes.

6. The device of claim 5, further comprising:

a plurality of tap lines extending into the aerosol container; and a device that selectively feeds aerosol-free gas into the tap lines.

7. The device of claim 4, further comprising:

a plurality of tap lines extending into the aerosol container; and a device that selectively feeds aerosol-free gas into the tap lines.

* * * * *

UNITED STATES PATENT AND TRADEMARK OFFICE

CERTIFICATE OF CORRECTION

PATENT NO. : 7,086,611 B2
APPLICATION NO. : 10/968836
DATED : August 8, 2006
INVENTOR(S) : Ingo Grausam It is certified that error appears in the above-identified patent and that said Letters Patent is hereby corrected as shown below:

Column 4

Line 10, before “nozzle” insert --at least one--

Signed and Sealed this

Seventeenth Day of October, 2006

JON W. DUDAS

*Director of the United States Patent and Trademark Office*